US008828729B1

(12) United States Patent
Natan et al.

(10) Patent No.: US 8,828,729 B1
(45) Date of Patent: Sep. 9, 2014

(54) METHODS AND APPARATUS FOR THE DETECTION OF TAGGANTS BY SURFACE ENHANCED RAMAN SCATTERING

(75) Inventors: Michael J. Natan, Los Altos, CA (US); Marcelo Eduardo Piotti, Freemont, CA (US)

(73) Assignee: Cabot Corporation, Boston, MA (US)

( * ) Notice: Subject to any disclaimer, the term of this patent is extended or adjusted under 35 U.S.C. 154(b) by 54 days.

(21) Appl. No.: 13/488,116

(22) Filed: Jun. 4, 2012

Related U.S. Application Data

(63) Continuation of application No. 12/695,952, filed on Jan. 28, 2010, now abandoned.

(60) Provisional application No. 61/147,997, filed on Jan. 28, 2009.

(51) Int. Cl.
*G01N 37/00* (2006.01)
*G01N 21/49* (2006.01)

(52) U.S. Cl.
CPC ............................. *G01N 21/49* (2013.01)
USPC .................... 436/56; 436/164; 427/7

(58) Field of Classification Search
None
See application file for complete search history.

(56) References Cited

U.S. PATENT DOCUMENTS

| | | | |
|---|---|---|---|
| 6,174,677 B1 | 1/2001 | Vo-Dinh | |
| 6,610,351 B2 * | 8/2003 | Shchegolikhin et al. | ......... 427/7 |
| 7,019,828 B2 | 3/2006 | Su et al. | |
| 7,400,395 B2 | 7/2008 | Chan et al. | |
| 7,564,548 B2 | 7/2009 | Flanders et al. | |
| 7,599,056 B2 | 10/2009 | Koo et al. | |
| 7,771,661 B2 | 8/2010 | Chan et al. | |
| 2010/0060893 A1 | 3/2010 | Norton et al. | |

OTHER PUBLICATIONS

Wikipedia, retrieved from internet: http://simple.wikipedia.org/wiki/Chemical_composition.*
Erb, et al., "Magnetic assembly of colloidal superstructures with multipole symmetry", Nature, Letters, vol. 457, Feb. 19, 2009, pp. 999-1002.
Insin, et al., "Incorporation of Iron Oxide Nanoparticles and Quantum Dots into Silica Microspheres", ACS Nano, 2007, pp. A-F.
Nagle, et al., "Templated Nanoparticle Assembly on the Surface of a Patterned Nanosphere", Nano Letters, 2003, vol. 3, No. 1, pp. 51-53.
Quinn, et al., "A SERRS-Active Bead/Microelectromagnet System for Small-Scale Sensitive Molecular Identification and Quantitation", Small Journal, 2007.

* cited by examiner

*Primary Examiner* — Robert Xu
(74) *Attorney, Agent, or Firm* — Swanson & Bratschun L.L.C.

(57) ABSTRACT

One embodiment is a SERS enhancing substrate which includes a porous substrate and a Raman enhancing material associated with a surface of the porous substrate. The Raman enhancing material may be a Raman enhancing metal or other Raman enhancing material. The Raman enhancing material may also be configured to improve binding of a taggant to the substrate. The substrate described above may be included in a sample vessel useful for the flow-through analysis of large sample volumes, or for the rapid analysis of very dilute samples. Other embodiments include methods and systems for detecting taggants with SERS and similar techniques.

7 Claims, 4 Drawing Sheets

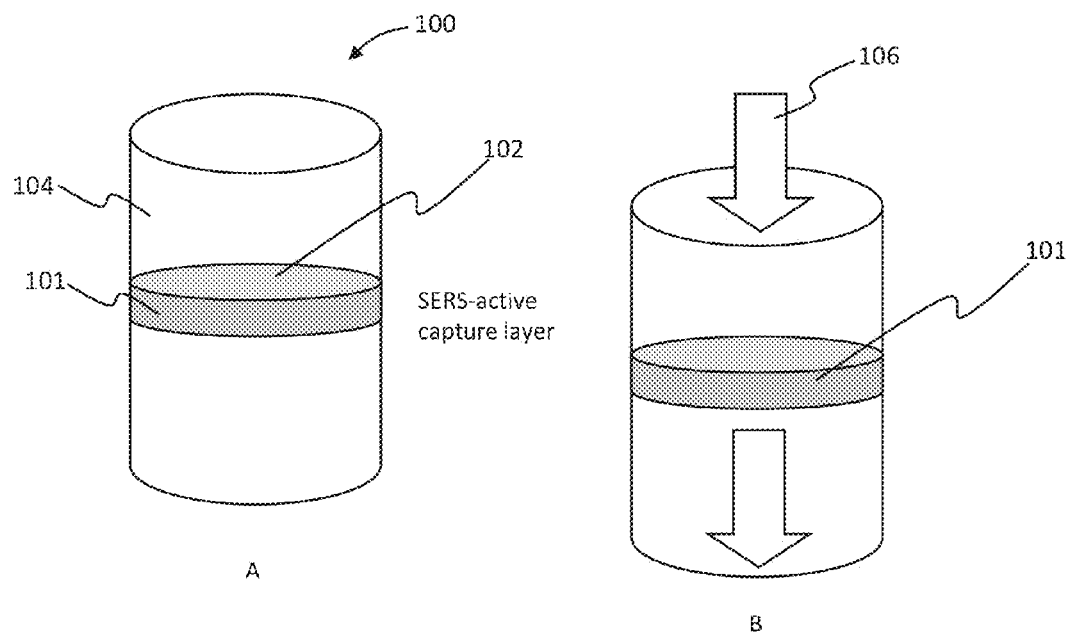
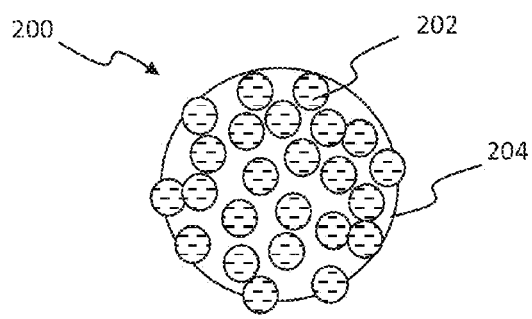
Fig. 1
Fig. 2

METHODS AND APPARATUS FOR THE DETECTION OF TAGGANTS BY SURFACE ENHANCED RAMAN SCATTERING

This application is a continuation of U.S. patent application Ser. No. 12/695,952, filed Jan. 28, 2010, which claims the benefit under 35 USC section 119 of U.S. Provisional Application No. 61/147,997 filed on Jan. 28, 2009, each entitled "Methods and Apparatus for the Detection of Taggants by Surface Enhanced Raman Scattering," the contents of which are hereby incorporated by reference in their entirety and for all purposes.

TECHNICAL FIELD

The disclosed embodiments include apparatus and methods to detect taggants. More specifically, the disclosed embodiments concern approaches to qualitatively or quantitatively determine the amount of a taggant using Raman scattering or surface enhanced Raman scattering (SERS).

BACKGROUND

Taggants are materials, substances, molecules, ions, polymers, nanoparticles, microparticles, or other matter, incorporated into, onto or otherwise associated with objects for the purposes of identification or quantitation. More specifically, taggants are used in activities and products including but not limited to detection, analysis, and/or quantification measurements related to brand security, brand protection, trademark protection, product security, product identification, brand diversion, barcoding, grey market remediation, friend-or-foe analysis, product life cycle analysis, counterfeiting, anti-counterfeiting, forensic analysis of authenticity, authentication, biometrics, object tracking, chain-of-custody analysis, product tampering, anti-smuggling, smuggling detection, supply-chain tracking, product tracking, lost revenue recovery, product serialization, serialized authentication, freshness tracking, sell-by date tracking, use-by date tracking, and standoff detection/identification.

Taggants can be added to all forms of matter, including but not limited to solids, liquids, gases, gels, foams, semi-solids, glasses, plasmas, liquid crystals, amorphous and magnetically-ordered solids, superconductors, superfluids, Bose-Einstein condensates, and supersolids.

The addition of taggants to liquids, and in particular liquid hydrocarbons such as fuel, diesel oil, gasoline, kerosene, ethanol, biodiesel, methanol, crude oil, fuel additives, etc. has been described in the prior art, and is recognized to be useful for a number of reasons. Similarly, the addition of a taggant allows protection against counterfeiting, or use of the hydrocarbon in an improper setting (i.e. brand diversion). Likewise, the ability to measure the concentration of a taggant in a hydrocarbon allows a determination of purity: if the concentration is lower than added, it suggests that the sample has been tampered with (for example by addition of a less valuable hydrocarbon). Often, this tampering can be at the level of a 1-5%, so highly accurate and precise measurements of taggants are required. Measuring taggant concentration can also be invaluable for process monitoring, where crude oil (for example) is often mixed with mud, steam, water, and other impurities, and where knowledge of the actual oil concentration impacts how selected processes are carried out. In another example, when fuel products with different owners share the same infrastructure (e.g. a pipeline), a tagged fuel allows operators to know which fuel is at which location at which time.

Likewise, addition of a taggant also provides insurance against legal liability. For example, the absence of taggant in a spilled sample of oil or gasoline allows fuel owners who have added taggant to their oil or gasoline to be exempt from liability. In many cases, the use of known taggants results in insufficient precision, detection accuracy or other problems.

Many known methods of detecting taggants utilize one of several spectroscopic techniques, for example a surface-enhanced spectroscopy (SES) techniques such as SERS or SERRS. An extraordinarily large number of SERS-active materials exist. Broadly speaking, suitable materials fall in two categories: nano-/microscale and macroscopic. For example, certain sizes and shapes of Ag and Au nanoparticles, and aggregates thereof, are known to support SERS. Likewise, a large variety of macroscopic SERS substrates have been described in the literature, including electrodes, evaporated films, Langmuir-Blodgett films, 2-dimensional planar arrays, and so forth.

A significant weakness of previously-described SERS substrates is their inability to accommodate large sample volumes, and more particularly function well with very dilute analytes in large sample volumes. Consider, for example, a sample volume of 100 mls in water, containing a molecule to be analyzed at concentration of $10^{-15}$ M. The total number of molecules is $10^{-16}$ moles, or 60 million, which is a substantial number. Nevertheless, this poses a substantial problem for conventional SERS in that most macroscopic substrates are of dimensions of a few $cm^2$ (or less), meaning the sample dimensions are large compared to the substrate dimensions. As a result, the number of molecules that come into contact with the substrate is very low per unit time, and even if there were irreversible adsorption, it may take hours to days for all molecules to reach the substrate surface.

Known prior art tagging methods which utilize SERS-active tags typically include a reporter molecule or dye with known SERS-active characteristics. For example, a known SERS-active chemical can be added as a dye to mark fuel and a subsequent SERS spectrum obtained when the SERS-active dye is associated with a SERS-active metal particle or substrate. Only a limited number of SERS active chemicals are known.

The present invention is directed toward overcoming one or more of the problems discussed above.

SUMMARY

One embodiment disclosed herein is a SERS enhancing substrate which includes a porous substrate material and a Raman enhancing material associated with a surface of the porous substrate. The Raman enhancing material may be a Raman enhancing metal associated with the substrate surface. The Raman enhancing material may also be configured to improve binding of a taggant to the substrate.

The substrate described above may be included in a sample vessel useful for the analysis of large sample volumes, or for the rapid analysis of very dilute samples. The sample vessel includes a vessel inlet and outlet such that a liquid sample may be intermittently or continuously flowed through the sample vessel. The sample vessel also includes a porous substrate as described above. The porous substrate will include a Raman enhancing material associated with a surface of the substrate. The Raman enhancing material may be a Raman enhancing metal or other Raman enhancing substance. The Raman enhancing material may also be configured to improve the binding of a taggant to the porous substrate.

An alternative embodiment includes a method of tagging a material or detecting a taggant. The method includes associating a SERS active taggant with a material of interest. The material of interest may be a liquid or associated with a liquid. The method further includes flowing the material and taggant through a porous SERS enhancing substrate and detecting a Raman spectrum of the taggant while associated with the SERS enhancing substrate.

Alternative embodiments include containers of any size or type having a SERS enhancing surface. In use, the containers may be used to hold or contain a sample tagged with a SERS active taggant.

Alternative embodiments include other method and apparatus for liquid or fuel tagging and methods, apparatus and compositions of matter useful for the indirect detection of a SERS taggant. Various indirect SERS detection methods feature a taggant which is initially either wholly or partially SERS inactive and which is used to tag a substance. Subsequently, a SERS active product is created or formed from the initial SERS inactive taggant and detected.

BRIEF DESCRIPTION OF THE DRAWINGS

FIG. 1 is a schematic diagram showing a porous SERS-active capture layer.

FIG. 2 is a diagram showing a hybrid magnetic SERS-active bead.

DESCRIPTION

Figure 3:
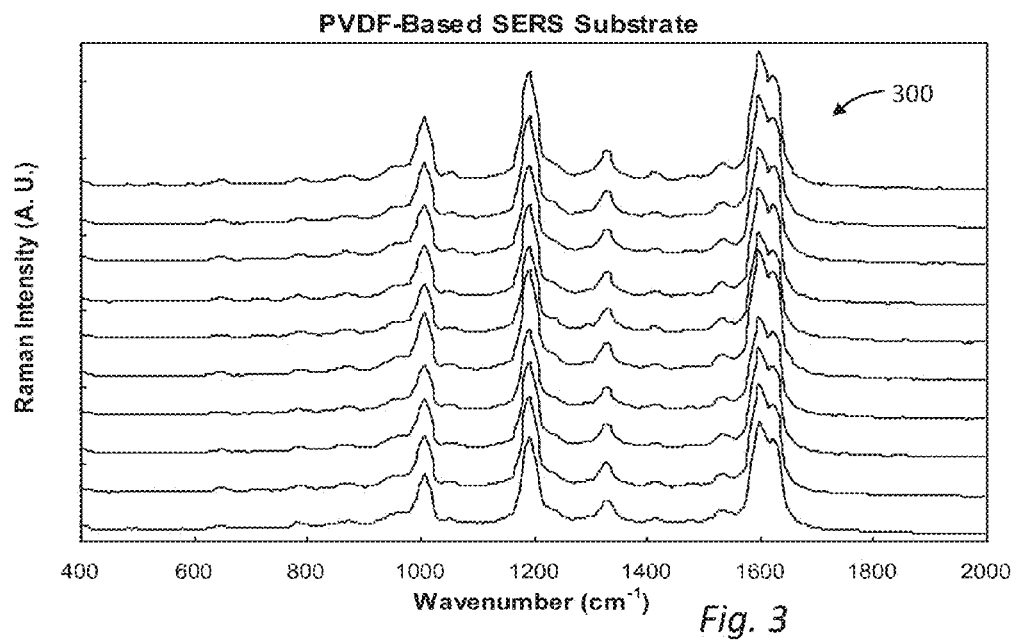
FIG. 3 is a graph of Raman intensity for a PVDF-based SERS substrate.

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Many of the embodiments disclosed herein relate to substances, materials or taggants that are spectroscopically active. In particular, several the disclosed materials and methods feature the use of a surface-enhanced spectroscopy (SES) active taggant. Representative SES techniques include but are not limited to SERS, SERRS and others. Surface enhancement in various other spectroscopy methods or systems has been observed. The most widely studied have been surface-enhanced Raman scattering and surface-enhanced fluorescence (SEF). But a variety of other surface enhanced phenomena have been observed including surface-enhanced hyper Raman scattering (SEHRS), surface-enhanced hyper Raman resonance scattering (SEHRRS), surface-enhanced Rayleigh scattering, surface-enhanced second harmonic generation (SHG), surface-enhanced infrared absorption reflectance (SEIRA), and surface-enhanced laser desorption ionization (SELDI). These are part of a wider field known as plasmon enhancement or plasmon-enhanced spectroscopy, which in addition to the phenomena mentioned above includes surface plasmon enhanced emission (such as SPASERS—surface plasmon amplification of spontaneous emission of radiation), plasmon enhanced diffraction, and plasmon enhanced optical transmission. Plasmon enhancement is also a method to increase the efficiency of solar cells. As used throughout this disclosure SES includes the above listed and any related or similar spectroscopic technique.

Many of the examples herein are described with respect to SERS. It must be noted however that the methods, compositions and materials disclosed herein are equally applicable to SERRS, SEHRS, SEF, SEHRRS, SHG, SEIRA, SPASERS, or other surface enhanced or plasmon enhanced SES technique.

I. SERS Substrates

One set of embodiments disclosed herein concerns substrates for surface enhanced Raman scattering (SERS). SERS describes the enhancement in Raman signal obtained from molecules in close proximity to certain metals such as Au, Ag, Cu, Al, and other metals that exhibit SERS activity in the uv, vis, near-IR or IR regions of the electromagnetic spectrum SERS was first described in the late 1970's, and is now very well understood both from theoretical and experimental perspectives.

An extraordinarily large number of SERS-active materials exist; broadly speaking, suitable materials fall in two categories: nano-/microscale and macroscopic. For example, certain sizes and shapes of Ag and Au nanoparticles, and aggregates thereof, are known to support SERS. Likewise, a large variety of macroscopic SERS substrates have been described in the literature, including electrodes, evaporated films, Langmuir-Blodgett films, 2-dimensional planar arrays, and so forth.

A significant weakness of previously-described SERS substrates is their inability to accommodate large sample volumes, and more particularly function well with very dilute analytes in large sample volumes. Consider, for example, a sample volume of 100 mls in water, containing a molecule to be analyzed at concentration of $10^{-15}$ M. The total number of molecules is $10^{-16}$ moles, or 60 million, which is a substantial number. Nevertheless, this poses a substantial problem for conventional SERS in that most macroscopic substrates are of dimensions of a few $cm^2$ (or less), meaning the sample dimensions are large compared to the substrate dimensions. As a result, the number of molecules that come into contact with the substrate is very low per unit time, and even if there were irreversible adsorption, it may take hours to days for all molecules to reach the substrate surface.

More typically, SERS substrates are designed to handle sample volumes of 5 microliters to 500 microliters. In many instances, measurements are made in a dry state, after the carrier liquid or solvent or matrix are evaporated off the surface, and clearly this approach is impossible with a large sample volume.

a. Flow-Through Detection with SERS Substrates

Improved SERS substrates and systems that can function with large sample volumes are disclosed herein. One example of a disclosed substrate is illustrated in FIG. 1. A detection system 100 includes a porous layer 101 that has been coated with a SERS-active material 102 is set into a container, channel or passageway 104 with open ends (for example a glass flask or tube). The SERS-active material could be Ag colloid, Au colloid, an Ag film, an Au film, or any other suitable SERS active material. The SERS selective material may further be selected to improve binding of the desired taggant. For example a hydrophobic SERS selective material may be used for improved partitioning. Similarly, thermo- or solvent-responsive SERS selective materials could be used which can swell/shrink to trap taggant. The SERS selective material may become SERS active upon binding a taggant as described below.

A liquid containing the taggant 106 is poured, flowed or otherwise applied onto the porous layer 101 and passes through (with or without the use of pressure) leaving some or all of the taggant molecules on the SERS-active material. The porous capture layer and captured taggant is then examined with a Raman spectrometer or similar SES technique.

In an alternative approach, the flow-through substrate may be part of an integrated Raman or other SES detection system and spectra may be collected as the taggant bearing liquid passes through the porous layer. The detected Raman or other spectral signal as a function of time may then be used to determine the amount of taggant present in the liquid.

The porous layer 101 could be configured for use a single time and disposed of. Alternatively, a cleaning solution back washing system or other method may be used to return the porous layer to its initial state, allowing further use. Although the porous layer 101 of the FIG. 1 embodiment is represented as a relatively thin disc associated with a cylindrical container 104, other physical or mechanical configurations are well within the scope of the disclosed embodiments. For example, the porous layer may be of any shape, thickness or geometric configuration. Similarly, the vessel or container 104 may have a size, shape and flow pattern selected from any number of alternatives to achieve specific detection rates and goals. In addition, although FIG. 1 illustrates a flow-through embodiment, and flow-through embodiments may, as described above, be advantageous in selected implementations, the scope of the disclosed embodiments are not limited to flow-through apparatus. For example, an alternate method to increase the volume of material that is easily analyzed utilizing an SES, for example a SERS substrate is to build the substrate into some or all of the walls or surfaces of a container. Over time, the material in the container comes into contact with the substrate and may then be detected. The size of the SERS substrate may be small, or of any size, limited only by the size of the container.

B. Assay with Hybrid Magnetic/SERS-Active Substrates

For the detection of taggants in fuel, a HMSERS bead 200 as shown in FIG. 2 may be made by attaching SERS-active nanoparticles 202 to a magnetic bead 204. The nanoparticles 204 may be Au colloid, Ag colloid, or other suitable SERS active nanoparticulate materials. The nanoparticles 202 may be attached to the bead 204 by chemical bonding, by electrostatic forces or other methods.

A taggant placed in a liquid (such as a fuel) may be brought into contact with the HMSERS bead material, leading to deposition of the taggant on the HMSERS bead material surface. A magnetic field may then be used to concentrate the magnetic particles. The particles may then be placed in a Raman spectrometer and the signal from the taggants is detected.

C. Liquid or Fuel Tagging

An alternative embodiment of the method of preparing a quantity of fuel or other liquid for subsequent identification includes mixing Raman active reporter molecules, including but not limited to a SERS active dye, directly into the fuel, but eliminates the need for a separate colloid addition to the fuel. In this alternative, the marked fuel may be placed on, flowed over or through or otherwise associated with a SERS-active substrate prior to detection of the Raman spectrum. As described herein, the SERS-active substrate could be mesoscopic or macroscopic. The SERS-active substrate could be an immobilized colloid, a SERS-active metal, a coated photonic lattice or any substance which will enhance a SERS signal when the marked fuel or other marked liquid is placed upon it. A representative suitable SERS-active substrate may be prepared by creating a photonic lattice of self-assembled silicon spheres. The spheres may be coated with gold or another Raman enhancing metal which may be excitation tuned to the desired SERS spectrum acquisition laser wavelength. Fuel or another liquid marked with a SERS-active dye may be drawn onto the substrate thus prepared. The marker which may constitute a SERS-active dye will become active in the vicinity of the Raman enhancing metal surface. The dye mixture thus associated with the substrate may be excited with an appropriate diode laser and a SERS spectrum acquired. The composition and preparation of a SERS-active substrate which is suitable for the implementation the described embodiments includes but is not limited to the specific materials described and listed above.

In an alternative embodiment, aggregated Au colloid may be coated with a polymer, making the material an OrgAu which is soluble in fuel. OrgAu is then added to a mixture of fuel and taggant including but not limited to a SERS active dye. The taggant binds to OrgAu and can then be detected. Centrifugation of the sample allows additional concentration of the OrgAu and taggant, improving the sensitivity of the measurement. The polymer may be designed to specifically bind the taggant, as well as provide solubility in the fuel.

II. Indirect Detection of Taggant

Known prior art tagging methods which utilize SERS-active tags typically include a reporter molecule or dye with known SERS-active characteristics. For example, a known SERS-active chemical can be added as a dye to mark fuel and a subsequent SERS spectrum obtained when the SERS-active dye is associated with a SERS-active metal particle or substrate. Examples of Molecules that might be useful as direct taggants include but are not limited to: thiophene, mercaptobenzene, 1,4-Phenylene diisocyanide, 1,4-Diethynylbenzene, 4-Aminobenzoic acid, pyridine, d5-pyridine (where d represents deuterium), pentafluoropyridine 4-Aminopyridine, 3-Pyridyl isothiocyanate, 5-(4-pyridyl)-1,3,4-oxadiazole-2-thiol 4,4'-dipyridyl, d8-4,4'-dipyridyl, Trans-1,2-Bis(4-pyridyl)-ethylene, 4-Azobis(pyridine) deuterated 4-Azobis (pyridine), Bis-pyridylethynyl Benzene, 1-[2-cyano-2(4-pyridyl)ethenyl]-4-[2-cyano-2(4-ethynylphenyl)ethenyl]-benzene, 1,4-Bis(2-methylstyryl)benzene, terthiophene Benzimidazole, Benzotriazole, 2-naphthalene thiol, 2-Quinolinethiol, 4(5'-azobenzotriazoyl)-3,5-dimethoxyphenylamine, 1-aminopyrene, Copper(II) 5,9,14,18,23,27, 32,36-octabutoxy-2,3-naphthalocyanine, Crystal Violet, Rhodamine 6G, IR-775.

Various embodiments are disclosed herein, however, where a SERS-inactive taggant is used to tag a substance. Subsequently, a SERS-active product is created or formed from the initial SERS-inactive taggant and detected. Thus, the universe of molecules, compounds or substances which may be used as taggants which are detected by surface enhanced Raman spectroscopy is greatly expanded. For example, the taggant may be used to generate a chemical or physical change that results in the creation or release of a molecule that is detected by surface enhanced Raman scattering according to any variation of the following simplified and generic reaction:

$$A(\text{SERS-inactive taggant}) + Y \rightarrow B(\text{SERS-active product})$$

The taggant could be a reactant, or it could be a catalyst for a reaction. The taggant might end up being incorporated into the molecule that is actually detected by SERS, or it could end up separate or distinct. Alternatively, the taggant could be SERS-active, but involved in creation of an entity that is more easily detected (either due to polarizability, extent or strength of adsorption, or other factors).

The indirect detection methods disclosed herein can be used with any nanoscale, microscale, macroscale SERS detection platform (including but not limited to particles, particle substrates, SERS vials, 96-well plates, lithographically-fabricated SERS-active materials, and evaporated substrates). Likewise, indirect detection methods can be used with any type of SERS-active composition, including but not limited to Au, Ag, Cu, Al, alloys, core-shell particles, and any other SERS-active composition.

A. Organic Nitrile as a Taggant

Organic nitriles and similar compounds are one representative example of a molecule or compound which can be used for indirect SERS-based tagging. It is important to note that organic nitriles and the other compounds described herein are representative but not limiting examples. The scope of the indirect taggant detection apparatus and methods disclosed herein is limited not by the nature of the molecule or compounds discussed but by the general concept of detecting some type of product of the original taggant material. For example, the reaction of organic nitriles with organic azides yields a disubstituted tetrazole. When 4-cyanopyridine reacts with alkylazide a pyridyl tetrazole is produced. The pyridyl tetrazole has a much larger SERS spectrum than either of the starting materials. The nitrile could be the molecule added to tag fuel for example, since azides are sensitive to UV light and heat. Reaction with the azide component leads to a species detectable by any suitable means, including but not limited to flow-through substrates and HMSERS as discussed above or any other suitable means. The example reaction may be accelerated by the addition of Zinc salts.

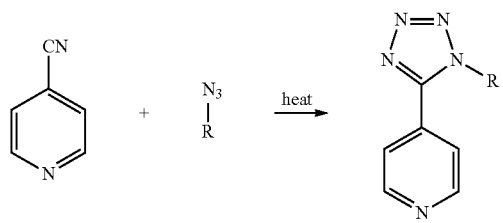

R=alkyl, aryl or H

B. The Use of an Alkyne as a Taggant

Similarly, the reaction of alkynes with organic azides forms triazoles. In particular the copper salt catalyzed reaction of alkyl azides with alkynes is regiospecific and occurs under mild conditions. Also, in this case, the ethynyl compound could be included in fuel due to the instability of azides.

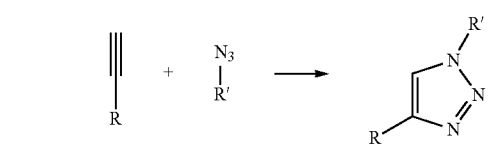

R, R' = alkyl or aryl

R, R'=alkyl or aryl

C. Generation of Resonant Molecules

In some cases the product of the reaction between a selected taggant and a reactant will be a molecule that is resonant with the excitation wavelength of the Raman spectrometer. Being resonant allows for surface enhanced resonance Raman scattering (SERRS), leading to a larger, more easily detected signal.

One non-limiting representative example of the resonance phenomenon described above is the reaction of $(bpy)_2RuCl_2$ with a third bipyridyl type ligand (including phenanthroline derivatives) which results in the formation of a hexacoordinated complex that has an absorption band at ~450 nm in a UV-vis spectrum. This absorption band is not present in the initial compound. This band could result in high SERS intensities when the compound is added to silver colloids due to the resonance effect. The formation of this resonance molecule can be used to develop a tagging method for fuels or other materials by adding a bipyridyl ligand (generically indicated by bpy*) to the tagged material. When the tagged material is mixed with a test kit containing $(bpy)_2RuCl_2$ then $(bpy)_2 bpy^*RuCl_2$ is formed, which in the presence of silver colloid could be detected by SERS using excitation at 514 nm or comparable wavelengths. This concept is illustrated below. The use of a 1,4-diethynyl phenanthroline molecule would be advantageous because the ethynyl group would help with the absorption of the complex to the metal surface.

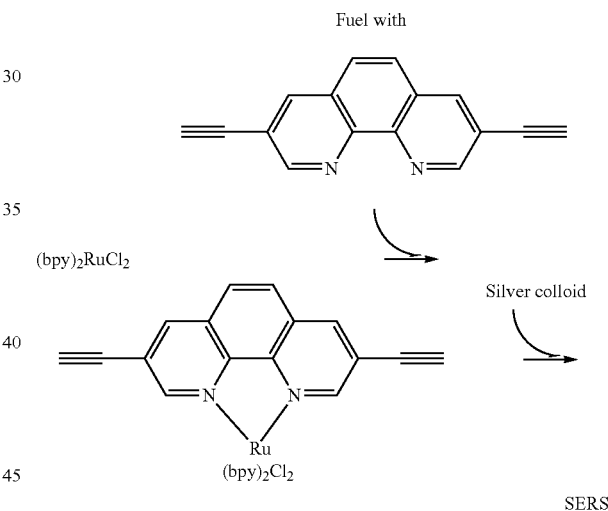

Formation and SERS Detection of Resonant Molecule During Fuel Test

D. Catalyst Formation

An alternative embodiment of indirect tagging includes the formation of any type of catalyst. For example, ruthenium complexes can become active catalysts for olefin cross metathesis when they react with a bulky and basic phosphine ligand. One example is tris-cyclohexylP ($Cy_3P$). To function as an indirect tag the fuel or other material may be tagged with $Cy_3P$. As shown below, the reaction with compound 1 gives compound 2. Compound 2 then reacts with an olefin having low SERS activity to produce a SERS-active molecule. A test kit would have the inactive Ru complex precursor and a non-SERS-active olefin. Once the phosphine tagged fuel or other material is added to the mixture, the catalyst is activated by ligand exchange, and the olefin is converted to the SERS-active compound. This compound is then detected by any method, for example, by association with one of many SERS surfaces.

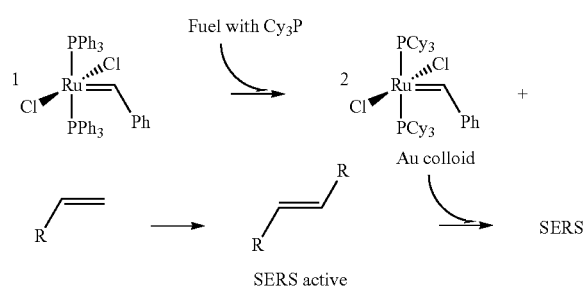

SERS Reporter Formation by Triggered Catalyst Activation

E. Enzyme Inhibitor

An alternative indirect method includes the use of an inhibitor. For example, a molecule that inhibits a particular enzyme can be added to a liquid sample, for example, oil. To analyze for the presence or absence or the amount of the taggant, a solution containing the enzyme may be mixed with a solution containing a substrate. The enzyme converts the substrate to a product. Either the substrate or the product may be SERS-active. At a selected point, the taggant-containing solution is added to this mixture, and enzyme inhibition occurs to an extent proportional to the concentration of inhibitor (taggant). Importantly, there exist enzymes that function in organic solvents or organic/aqueous mixtures, so that if the liquid to which the taggant is added is non-aqueous (e.g. oil or gas), it is still possible for the enzyme to retain its intrinsic activity (in the absence of inhibitor).

F. Enzyme Cofactor

Similarly, the taggant can be a co-factor or co-enzyme. Such a species may not be SERS-active by itself. However, when mixed with an apoenzyme, an (active) holoenzyme may be generated, and the holoenzyme can be used to convert substrate molecules to product molecules. If the product molecules are SERS-active, significant signal amplification has occurred, insofar as each co-factor can generate thousands to millions of product molecules, depending on the holoenzyme's turnover number (i.e. catalytic efficiency). Co-factors and co-enzymes may, for example, be metal ions or organic molecules or metal ions complexed to organic molecules.

G. Heat Stable Taggants

In some applications, the taggant needs to survive high temperature before being interrogated. For example, this might occur for items that are designed to be combusted in use. Molecules that are synthesized at relatively high temperatures are the best candidates to be stable at high temperatures. Examples include, but are not limited to, $Ru(bipy)_3$ and similar compounds, and Benz[g]isoquinoline-5,10-dione.

H. Unlaunderable Taggants

In certain cases, taggants in hydrocarbons that are SERS-active might adsorb to surfaces other than the SERS substrate. For example, conventional SERS-active taggants added to crude oil might adsorb to rocks or clay. Even container walls are possible adsorption sites. In general, the more soluble a conventional SERS taggant is in hydrocarbon, the lower its affinity for adsorption at SERS-active substrates. Thus, it would be desirable to be able to control the solubility of a taggant such that it is highly soluble in hydrocarbon, but prior to analysis or detection, binds strongly to a selected SERS-active substrate. One approach to achieve these goals is to modify SERS-active molecules with hydrocarbon tails, and then cleave the tails during analysis. For example, a taggant like 4,4' bipyridine (A) can be modified with an ester, for example, ($-CH2O(OC)(CH2)9CH_3$ group) in the 2 and/or 5' positions, rendering it hydrocarbon soluble. As a result, the molecule does not adsorb to any surfaces, and is thus not launderable or scavengable from a hydrocarbon solution. Likewise, it is not SERS-active, as it will not adsorb to a SERS-active surface. Prior to or during the analysis step, the taggant may be de-esterified by treatment with strong acid or strong base. The long alkyl chain is cleaved, and the molecule thus becomes SERS-active.

I. Background Reduction

Often, the identity and Raman spectra of fuel (or other tagged material) components may be known. Identification of the taggant can be improved by subtracting the Raman spectra of the fuel components from the acquired spectrum. Thus, when the fuel composition is known, Raman signals from the fuel can be used as internal references, allowing improved quantitation. In some cases the SERS result may not provide enough precision for the user. In those cases where taggant is found, mass spectrometry or another supplemental analysis technique can be used for better quantitation.

EXAMPLES

The following examples are provided for illustrative purposes only and are not intended to limit the scope of the invention.

Example 1

Preparation and Use of a Flow-Through Substrate

A substrate was prepared from a hydrophobic PVDF membrane, though many different materials may function in a similar manner. The membrane was cut to size and inserted into a 47 mm vacuum filtration apparatus, supported by a glass frit. After wetting the membrane with ethanol, 10 mL of 0.01% (w/v) colloidal gold, approximately 90 nm in diameter, was added on top of the filter. Vacuum was applied, and the colloidal gold stuck to the membrane, giving it a brownish-red appearance. To demonstrate the applicability of the substrate, 1 µM taggant (BPE: trans-1,2-Bis(4-pyridyl)ethylene) in n-octane was analyzed. The vacuum was removed, and 2 mL of the solution was added to the filter. Vacuum was applied and held for approximately 30 seconds. The filter was then removed from the vacuum apparatus and the SERS spectrum of BPE acquired at 10 separate locations using a Raman spectrometer and 785 nm laser for excitation. Resulting spectra 300 are shown in FIG. 3; these spectra have been offset for clarity.

Example 2

Preparation and Use of a Container Substrate

Figure 4:
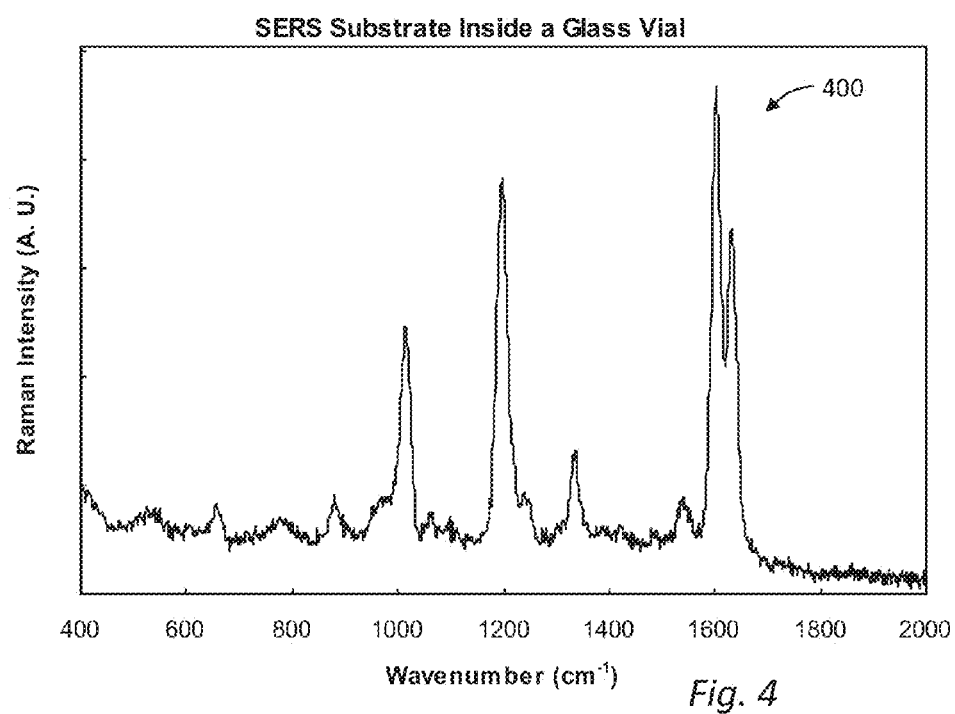
FIG. 4 is a graph of Raman intensity for a SERS substrate inside a glass vial.

A glass vial may be converted into a SERS substrate and used for convenient analysis of taggants in fuel or other typically liquid substances. 2 mL glass sample vials were acid-cleaned, then modified with 3-aminopropyltrimethoxysilane (APTMS) using standard methods, followed by profuse water rinses. 1 mL of 0.01% (w/v) colloidal gold, diameter 90 nm, was then added to the vial and incubated overnight. Gold nanoparticles are bound to the APTMS, resulting in a SERS substrate. Excess gold was removed by rinsing with water and ethanol. A 1 mL aliquot of n-octane containing 1 µM taggant (BPE: trans-1,2-Bis(4-pyridyl)ethylene) was added to the vial. After allowing a few minutes for taggant to bind to the SERS substrate, a spectrum was recorded using a conventional 785 nm Raman spectrometer. A spectrum 400 as shown in FIG. 4 was recorded directly through the bottom of the vial without removal of the sample.

Example 3

Fuel Tagging and Detection

Figure 5:
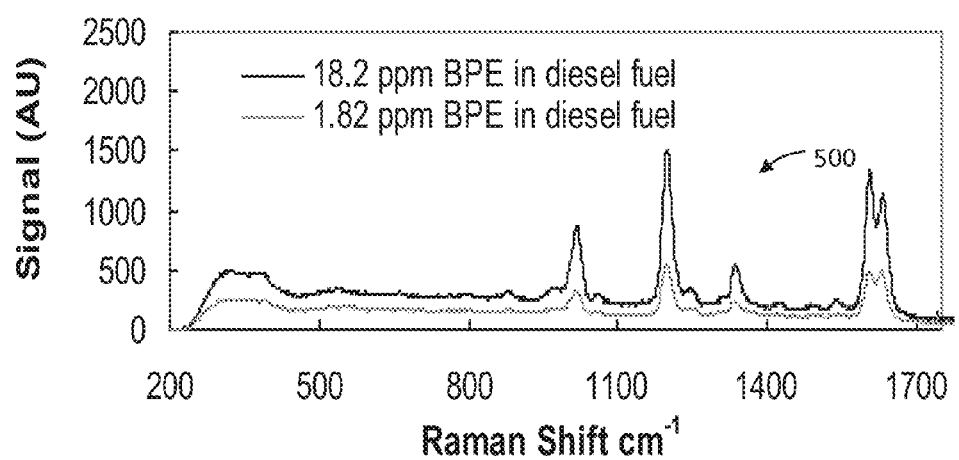
FIG. 5 is a graph of Raman intensity for a taggant in diesel fuel.

Colloidal gold may be used to detect a doped Raman reporter in diesel fuel. In this example, BPE Raman reporter molecules were doped into 2 separate diesel fuel samples. An 18.2 ppm sample was prepared by mixing 900 μl diesel fuel and 100 μl 1 mM BPE in ethanol in a glass vial. Also, a 1.82 ppm sample was prepared by mixing 990 μl diesel fuel and 10 μl 1 mM BPE in ethanol in a separate vial. The addition of 200 ul (0.010% (w/v)) 60 nm Au colloid in water was vortexed into each sample. Inverting the vials a few times collected the water bubbles from the hydrophobic fuel into a single layer at the bottom of the vial. The Raman reporter molecules were extracted from the fuel through the mixing and observed to bind to the gold in the aqueous layer. As shown in the spectra 500 of FIG. 5, the bound reporter molecules were signal enhanced by SERS and the SERS spectra 500 were acquired using a 785 nm laser read through the aqueous layer from the bottom of the vial.

Example 4

Formation of HMSERS Particles

Figure 6:
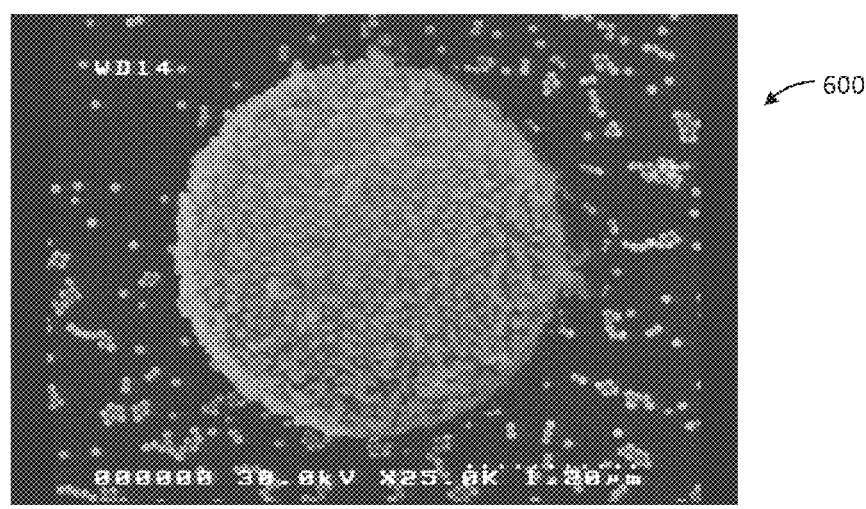
FIG. 6 is a SEM image of a magnetic bead coated with Au colloid.

FIG. 6 is an SEM image of a HMSERS particle 600 formed as described below. 900 mL of Au colloid was concentrated by centrifugation to a volume of 90 mL and particle concentration of approximately $4.6 \times 10^{14}$ particles/L. 250 μL Dynal 2.8 um diameter (amino coated) magnetic beads were washed 3 times in water and resuspended in 1 mL of water. In a square plastic Nalgene bottle, washed magnetic beads were added in small aliquots (~50 ul at a time) while mixing to the concentrated colloid. The colloid and bead mixture was allowed to react on a plate shaker overnight at room temperature. The mixture was removed from the plate shaker and allowed to react on a bench top for at least 4 days. Before use, excess Au colloid was removed by centrifugation and washing.

Example 5

Detection of Taggant in Fuel with HMSERS Particles

Figure 7:
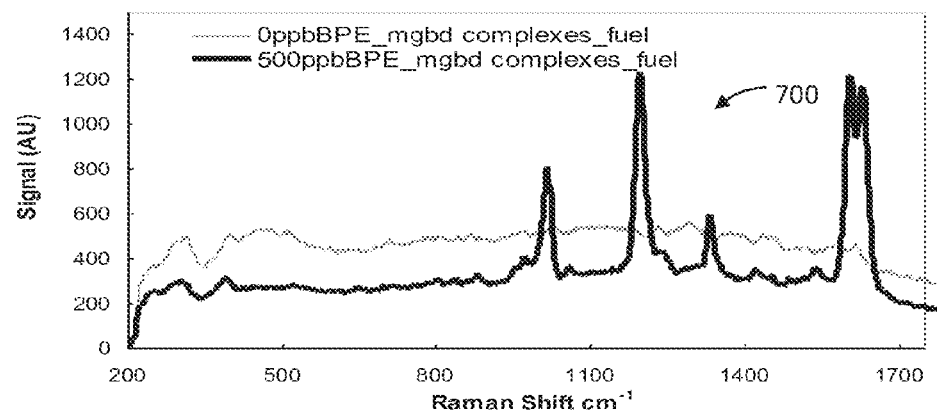
FIG. 7 is a graph of Raman intensity for a taggant in fuel.

Colloidal gold coupled to magnetic beads formed as described in Example 4 was used to detect a taggant molecule (BPE: trans-1,2-Bis(4-pyridyl)ethylene) in diesel fuel. A 500 ppb BPE sample was prepared by mixing 998 μl diesel fuel and 2.75 μl 1 mM BPE in ethanol in a glass vial. A separate sample was prepared containing no BPE. 40 μL of colloidal gold coated magnetic particles (in water) and 40 μl water were added to each of the samples. The samples were vortexed for mixing and inverted, allowing an aqueous layer to form below the fuel layer. Inverting the vials a few times collected the water bubbles from the hydrophobic fuel into a single layer at the bottom of the vial. The aqueous layer was also observed to contain the HMSERS particles, now coated with taggant. Thus, the taggant molecules were extracted from the fuel during the mixing step and bound to the gold coated magnetic beads in the aqueous layer. The fuel layer was removed while the water layer (containing HMSERS particles) was transferred to a 0.2 ml Axygen tube. A magnet was used to concentrate the HMSERS particles and as illustrated in FIG. 7, the SERS spectra 700 were acquired using a 785 nm laser read through the sidewall of the tube.

Example 6

Indirect Detection

4-Cyanopridine was added as a taggant in isooctane at 0.1% concentration. Subsequently, 152 mg of sodium azide (2.35 mmol) and 472 mg of zinc bromide (2.1 mmol) were mixed in 10 ml of 1/1 water/i-PrOH. 1 ml of the cyanopyridine solution in isooctane was added and the resulting mixture was refluxed overnight under vigorous stirring as shown below. After cooling down, 10 ml of the resulting solution was added to 1 ml of 60 nm gold colloid and SERS was monitored. The spectrum of the corresponding tetrazole was observed.

As a control experiment, the sodium azide and zinc bromide were refluxed in the water/i-PrOH mixture for the same amount of time. When 10 ul of the resulting solution was added to 1 ml gold colloid, no SERS is observed.

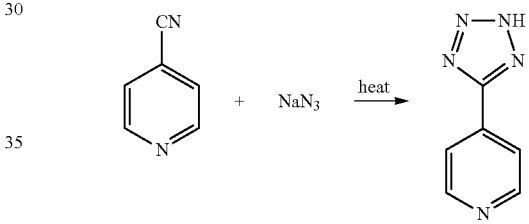

Various embodiments of the disclosure could also include permutations of the various elements recited in the claims as if each dependent claim was multiple dependent claim incorporating the limitations of each of the preceding dependent claims as well as the independent claims. Such permutations are expressly within the scope of this disclosure.

While the disclosed embodiments have been particularly shown and described with reference to a number of examples, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

The description of the embodiments has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A method of tagging a substance comprising:
    associating a SERS-active taggant with the substance;
    modifying the SERS-active taggant to form a SERS-active product having a different chemical composition and a different SERS spectrum than the SERS-active taggant; and
    detecting the SERS spectrum of the SERS-active product, wherein the SERS active product has different polarization than the SERS-active taggant and wherein the SERS-active taggant is a phenanthroline derivative, the method further comprising reacting the phenanthroline derivative with a bipyridyl ligand to form the SERS-active product.

2. The method of claim 1 wherein the SERS active product has different spectroscopic adsorption strength than the SERS-active taggant.

3. The method of claim 1 wherein the SERS active product is resonant with the excitation wavelength of a Raman spectrometer used to detecting a SERS spectrum of the SERS-active product.

4. The method of claim 1 wherein the bipyridyl ligand comprises (bpy)2RuCl2.

5. The method of claim 1 wherein the phenanthroline derivative comprises 1,4-diethynyl phenanthroline.

6. The method of claim 1 further comprising detecting the SERS spectrum of the SERS-active product by using a SERS excitation wavelength of 514 nm.

7. The method of claim 1 wherein the substance is a fuel.

* * * * *